United States Patent
Haimerl et al.

(10) Patent No.: US 8,594,397 B2
(45) Date of Patent: Nov. 26, 2013

(54) JOINT RECONSTRUCTION PLANNING USING MODEL DATA

(75) Inventors: Martin Haimerl, Gilching (DE); Mario Schubert, Poing (DE)

(73) Assignee: Brainlab AG, Feldkirchen (DE)

( * ) Notice: Subject to any disclaimer, the term of this patent is extended or adjusted under 35 U.S.C. 154(b) by 473 days.

(21) Appl. No.: 12/433,912

(22) Filed: May 1, 2009

(65) Prior Publication Data

US 2009/0285465 A1    Nov. 19, 2009

Related U.S. Application Data

(60) Provisional application No. 61/056,882, filed on May 29, 2008.

(30) Foreign Application Priority Data

May 15, 2008    (EP) .................................... 08156279

(51) Int. Cl.
    *G06K 9/18*    (2006.01)
(52) U.S. Cl.
    USPC .......................................... 382/128; 382/131
(58) Field of Classification Search
    USPC ................................................. 328/128, 131
    See application file for complete search history.

(56) References Cited

U.S. PATENT DOCUMENTS

| 5,871,018 | A | 2/1999 | Delp et al. |
| 8,014,984 | B2 * | 9/2011 | Iannotti et al. ..................... 703/6 |
| 2005/0267353 | A1 | 12/2005 | Marquart et al. |
| 2008/0221700 | A1 * | 9/2008 | Howald et al. ............. 623/23.12 |

FOREIGN PATENT DOCUMENTS

| EP | 1124201 A1 * | 8/2001 |
| EP | 1 693 798 | 8/2006 |
| WO | 00/63844 | 10/2000 |

OTHER PUBLICATIONS

Nötzli et al., "The contour of the femoral head-neck junction as a predictor for the risk of anterior impingement", The Journal of Bone & Joint Surgery (Br), 2002 84-B, pp. 556-560.
Ashburner et al., "Image Segmentation", The Wellcome Dept. of Imaging Neuroscience, Chapter 5, 2003, pp. 1-16.
Jepson et al., "Image Segmentation", 2007, pp. 1-34.

* cited by examiner

*Primary Examiner* — Joseph Chang
*Assistant Examiner* — Jeffrey Shin
(74) *Attorney, Agent, or Firm* — Renner, Otto, Boisselle & Sklar, LLP

(57) ABSTRACT

The invention relates to a computer-assisted planning method for reconstructing changes in shape on joint bones, comprising the following steps:
   a three-dimensional patient data set is acquired;
   reconstruction-type model data is assigned to the patient data set;
   resection auxiliary regions are determined by means of the model data; and
   the resection auxiliary regions are visually output and/or visualized together with the patient data set.

28 Claims, 1 Drawing Sheet

JOINT RECONSTRUCTION PLANNING USING MODEL DATA

RELATED APPLICATION DATA

This application claims the priority of U.S. Provisional Application No. 61/056,882, filed on May 29, 2008, which is hereby incorporated in its entirety by reference.

FIELD OF THE INVENTION

The invention relates to the field of joint reconstruction planning; in particular, it relates to a computer-assisted planning method for reconstructing changes in shape on joint bones.

BACKGROUND OF THE INVENTION

Changes in the shape of joint bones are a possible cause of arthritic joint ailments. For example, bone anomalies can arise in the region of the hip joint which lead to bone collisions in the region of the joint when the leg is moved and—in particular over a longer period—cause attrition. In order to prepare reconstruction treatments, i.e. treatments which restore a suitable shape of the bone, planning is necessary which can be performed with computer assistance. The reshaping of the femoral head, and sometimes of the rim of the joint cavity, is planned in such a way that unnatural collisions between the femoral bone and the acetabulum (joint cavity) in the joint environment are prevented, wherein a natural shape of the femoral head is to be achieved. The basis of such planning has previously been to determine the contour of joint bones on a two-dimensional basis, for example in a particular sectional plane or imaging plane. In the "Journal of Bone and Joint Surgery", volume 84-B, No. 4, May 2002, pages 556 to 560, Noetzli et al. describe determining the contour of a femoral neck, for which a measuring and angle system is specified, to which reference shall also be made later in this document.

SUMMARY OF THE INVENTION

It is the object of the present invention to enable joint reconstruction planning which enables a sufficiently accurate reconstruction at little expense. The intention is in particular to avoid elaborate and lengthy image processing operations, in order to enable planning to be more flexibly used.

This object is solved by a computer-assisted planning method for reconstructing changes in shape on joint bones, comprising the following steps: a three-dimensional patient data set is acquired; reconstruction-type model data is assigned to the patient data set; resection auxiliary regions are determined by means of the model data; and the resection auxiliary regions are visually output and/or visualized together with the patient data set. The sub-claims define preferred embodiments of the invention.

In other words, the present invention uses model data which is suitable for the upcoming bone reconstruction, in order to be able to deduce the abrasion or resection regions by processing such model information. Such model data, which can be model image data, can easily be processed and linked to the patient data set, in particular an image data set, and this also leads to quick results, in particular without the content of a patient image data set having to be elaborately analyzed. For in such analyses, the properties of the elements to be imaged, their identity and their delineation with respect to other elements are deduced from the image material; this process is called segmentation. Segmentation is computationally very elaborate, and the corresponding planning steps therefore take a relatively long time. If segmentation steps can be omitted with the aid of the model data, this enables planning to be more flexibly used and also to be adapted and changed. It is also in particular possible to plan intra-operatively using intra-operative image recordings (CT, MR). Another advantage of eliminating segmentation is that segmentation is often very difficult when image data sets of joint environments are produced. Usually, MR (magnetic resonance tomography) images are produced, because soft tissue defects play a major role in the ailments in question. However, it is very difficult to clearly segment bone structures in MR data, and for this reason too, the use in accordance with the invention of reconstruction-type model data for determining the resection auxiliary regions and ultimately the resection regions themselves is highly advantageous with respect to the prior art.

The patient data set used can be:
an image data set of the joint bone environment, which is produced by means of a medical imaging method; or
a surface model of the joint bone, which has in particular been tapped or scanned using a registered tool (for example, pointer scanning or light/laser scanning);
or a combination of these.

The patient data set, specifically the image data set, can be positionally registered, wherein reference coordinate systems or direction information are in particular determined and/or planned in the data set. Pointer scans using a pointer which is registered in the tracking/navigation system result in the surface model being registered automatically.

The imaging method can be a computer tomography method, a magnetic resonance tomography method or an x-ray method, specifically with volume detection.

In accordance with the invention, it is possible to plan the reconstruction on a medical navigation system which is provided with the patient data set, specifically the image data set, and the model data set. The resection regions can then be visualized on an image output of the navigation system.

In one embodiment of the invention, one or more of the following items of information are planned and/or determined as the reference coordinate systems and/or direction information: the femoral neck axis, the mechanical femoral axis, the centre point of the femoral head, the radius of the sphere of the femoral head, the posterior condylar axis, the epicondylar axis, pelvic planes, in particular the mid-sagittal and/or front pelvic plane, and the acetabular plane. With even only some of this information, it is possible to inscribe a sphere into the femoral head, and the abrasion and/or resection regions can already be at least partially localized or defined.

The model data is in particular assigned to the patient data set, specifically to the image data set, by computer-assisted superimposing and/or by matching elements of the model data and elements from the joint bone data and/or joint bone image data which substantially correspond in terms of their shape.

Resection regions which result from at least some of the impingements between the resection auxiliary regions and the acquired patient data set of the joint bone can form the basis for reconstruction planning. When determining the resection regions, the model data itself can also be taken into account as a partial region or excluded partial region, i.e. in this case, model data such as has been described above (for example, the radius of the sphere of the femoral head) would also for example additionally be used to localize the resection regions which are ultimately to be located.

The aforementioned model data can include data of the following nature:
- basic geometric shapes, in particular spheres, spherical hollow bodies, cylinders, saddle shapes or combinations of these;
- axes, areas, centre points, circumferences and edges, and points or areas of them;
- angular ranges, in particular having their origins at predetermined or characteristic centre points, axial points or surface points, specifically α and/or β angles in accordance with Noetzli et al.; and
- standardized reference data for the joint, in particular reference model data; or can be composed of several of the aforesaid data.

In order to optimize planning, the reference data can be corrected, wherein it would be corrected on the basis of joint-type or joint bone-type data, for example antetorsion angles, retroversion angles, CCD angles, location of the front/mid-sagittal pelvic plane, or pelvic inclination. It is also possible to automatically select a suitable reference data model on the basis of the acquired patient data set.

The method in accordance with the invention can specifically be used for a hip joint, a shoulder joint or a knee joint, but can in principle be used for any joints and joint environments.

In accordance with another aspect, the invention also relates to a program which, when it is running on a computer or is loaded on a computer, causes the computer to perform a method such as has been illustrated above in the different embodiments. It also relates to a computer program storage medium which comprises such a program.

BRIEF DESCRIPTION OF THE DRAWINGS

The invention is illustrated below in more detail on the basis of embodiments and optional enhancements and by referring to the enclosed drawings. It can include any of the features described here, individually and in any expedient combination.

DETAILED DESCRIPTION

Figure 1:
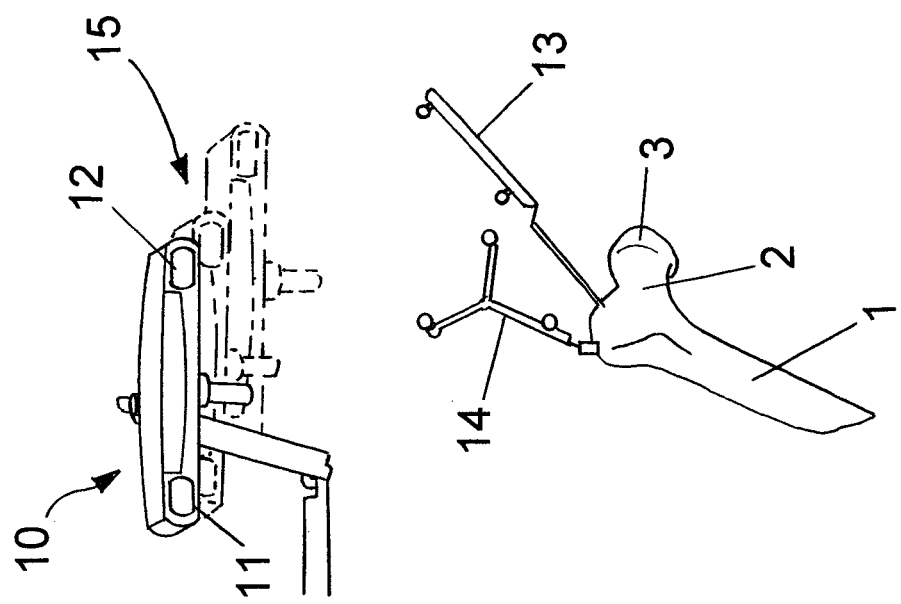
FIG. 1 shows a schematic representation of a joint bone, within the environment of a medical tracking system.

FIG. 1 schematically shows how an upper part of a femoral bone can be positionally located and tracked and/or registered with the aid of a medical tracking system 10. The tracking system 10 comprises two cameras 11 and 12 which can track the position of specific markers. Such markers are for example situated on the reference star 14 or on the pointer 13, which are shown in the lower part together with the image of the femoral bone 1, on which the femoral neck 2 and femoral head 3 can be seen.

The reference star 14 is fixedly connected to the femur 1. Because an image data set of the femur 1 has been produced beforehand, it is then possible to positionally assign this image data set to the femoral bone 1 via the reference star 14, i.e. to register the femoral bone. Therefore, the location of specific reference coordinates is then known, and direction information is also available, for example via the location of the femoral axis, the neck axis or the centre point of the head 3. It is possible to move the pointer 13 to specific points on the surface of the bone 1; however, the pointer here can also represent any other navigable instrument (tool).

Figure 2:
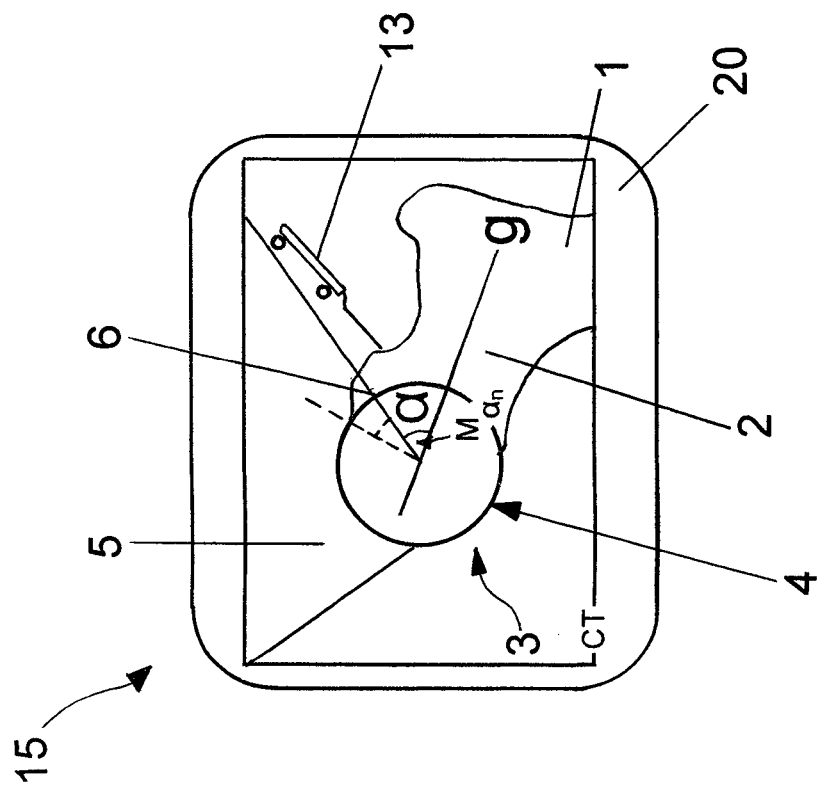
FIG. 2 shows a screen output of a planning system in accordance with the invention.

FIG. 2 shows an image output of a navigation system, using which planning in accordance with the invention is performed. In both drawings, the navigation system (comprising the tracking system and the screen output) is schematically indicated by the reference sign 15; the computational unit is not separately shown, but is usually provided.

The femoral bone 1 and the femoral neck 2 can in turn be seen on the image output 20 in a two-dimensional representation. The femoral head 3 is obscured by the inscribed sphere (the circle in the two-dimensional representation) 4. The centre point of the sphere is designated by M and coincides with the centre point of the femoral head. The neck axis bears the designation g. The angle α, which is derived from the measuring and/or angle system in accordance with Noetzli et al. mentioned at the beginning, is the angle between the neck axis g and the radial ray which runs from the centre point M, through the point on the circle at which the bone contour first deviates from the spherical shape. The angle $α_n$ then designates the angle between the neck axis g and the radial ray at which the bone can normally be present at the circle. Using the angles α and $α_n$, the neck axis g, the centre point M and the sphere (circle), it is possible to define a resection auxiliary region 5, and the resection region 6 can be ascertained from the impingements, without the image data set from which the representation 20 is derived having to be segmented.

In one embodiment in accordance with the invention, reference coordinate systems or direction information are firstly planned in the image data set for this purpose, i.e. preferably the neck axis g, the mechanical femoral axis, the centre point of the femoral head, and the radius of its sphere. Referencing and/or registration is performed via an attached reference 14. It is also possible to perform CT-fluoroscopic matching using a C-arm x-ray apparatus in situ, or any other registration. Optionally, any other model information can of course also be planned or taken into account, in particular other bone axes or bone areas. In accordance with the reference coordinate system and/or direction information, basic planning in accordance with standardized models is then possible (for example, a angles, a more detailed analysis of the usual bone anatomies and their relationship in the event of collision and/or impact problems). The abrasion regions (resection regions) can be defined from this information, and the construction of these areas is based on the rays which are emitted from the femoral head and defined in terms of their direction by the standardized models. In FIG. 2, for example, these rays define the resection auxiliary region 5.

The abrasion or resection regions or—conversely—the non-abrasion regions can then be visualized in two-dimensional views of the image data set recorded pre-operatively or also intra-operatively. In FIG. 2, the abrasion area is given by the amount of intersection between the bone 1 in the region 3 and the resection auxiliary area 5, less the circular area 4, as the resection area 6. The bone tissue in the region of the resection area 6 can be removed, in order to give the bone its desired condition.

When this resection and/or abrasion is planned in accordance with the invention, the actual operative activity can be visually assisted with the aid of navigation.

Other optional and/or advantageous developments of the method in accordance with the invention are discussed below. Thus, for example, a data fusion between pre-operative data sets comprising planning information (for example, segmented CT or MR data sets) and intra-operative data (for example, intra-operatively acquired MR data) can be performed. It is also possible to generate a rough 3D model (for example, from only a few reference points or reference axes/planes, etc.) and use it for visualization tasks. Another option is to use a rough segmentation as an aid in the navigation process, for example for CT/MR-fluoroscopic matching or for three-dimensionally visualizing the bone using volume rendering techniques. Such rough segmentations can be sufficient for this purpose, but can nonetheless be used quickly and flexibly enough (as opposed to the detailed segmentations otherwise used).

It is possible to make corrections in accordance with different alignments of the femoral bone (antetorsion angle, CCD angle) and of the pelvis (for example, inclination, anteversion/retroversion of the acetabulum). This is useful because some standard techniques rely on restrictive assumptions with respect to the anatomy. The α angle, for example, only considers the neck axis. However, an approach which is based on an actual range of motion also has to take into account the antetorsion, CCD angle, inclination, etc.

Although it has been described here in the example embodiment on the basis of a femoral head, navigation planning in accordance with the invention and navigation based on it can also be used on the "opposite side", i.e. on the acetabulum or joint cavity side.

It is also possible to reconstruct the local bone structure surfaces, in order to more accurately define the abrasion and/or resection regions. It is for example possible to tap the surface of the head-neck bond with a pointer and digitize the tapped points. FIG. 2 shows the pointer 13 during this operation. This surface can then be used to define the abrasion volume in detail. The information of the digitized points and the image data set information can also be combined.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A computer-assisted planning method for reconstructing changes in shape on joint bones, comprising the following steps:
   acquiring a non-segmented three-dimensional patient data set;
   directly assigning reconstruction-type model data to the patient data set;
   determining, using a processor, resection auxiliary regions by means of the model data; and
   visually outputting the resection auxiliary regions and/or visualizing the resection auxiliary regions together with the patient data set.

2. The method according to claim 1, wherein the reconstruction-type model data is model image data.

3. The method according to claim 1, wherein the patient data set comprises at least one of:
   an image data set of the joint bone environment, which is produced by means of a medical imaging method; or
   a surface model of the joint bone.

4. The method according to claim 3, wherein the surface model of the joint bone is obtained by identifying surface points via a trackable tool.

5. The method according to claim 3, further comprising positionally registering.

6. The method according to claim 5, wherein the image data set is the patient data set.

7. The method according to claim 5, further comprising determining or planning reference coordinate systems or direction information in the data set.

8. The method according to claim 3, wherein the imaging method is a computer tomography method, a magnetic resonance tomography method or an x-ray method.

9. The method according to claim 8, wherein the imaging method is a method with volume detection.

10. The method according to claim 1, further comprising planning the reconstruction on a medical navigation system which is provided with the patient data set and the model data set.

11. The method according to claim 10, wherein the image data set is the patient data set.

12. The method according to claim 10, further comprising visualizing the resection regions on an image output of the navigation system.

13. The method according to claim 1, wherein one or more of the following items of information are planned and/or determined as the reference coordinate systems and/or direction information: the femoral neck axis, the mechanical femoral axis, the centre point of the femoral head, the radius of the sphere of the femoral head, the posterior condylar axis, the epicondylar axis, pelvic planes and the acetabular plane.

14. The method according to claim 13, wherein the pelvic planes are the mid-sagittal or front pelvic plane.

15. The method according to claim 1, wherein directly assigning includes assigning the model data to the patient data set by computer-assisted superimposing and/or by matching elements of the model data and elements from the joint bone data and/or joint bone image data which substantially correspond in terms of their shape.

16. The method according to claim 15, wherein the image data set is the patient data set.

17. The method according to claim 1, further comprising determining resection regions which result from at least some of impingements between the resection auxiliary regions and the acquired patient data set of the joint bone as the basis for reconstruction planning.

18. The method according to claim 17, wherein determining the resection regions includes using the model data is as a partial region or excluded partial region.

19. The method according to claim 1, wherein the model data includes at least one of the following types of data:
    basic geometric shapes;
    axes, areas, centre points, circumferences and edges, and points or areas of them;
    angular ranges; or
    standardized reference data for the joint.

20. The method according to claim 19, wherein the basic geometric shapes are spheres, spherical hollow bodies, cylinders, saddle shapes or combinations thereof.

21. The method according to claim 19, wherein the angular ranges have their origins at predetermined or characteristic centre points, axial points or surface points.

22. The method according to claim 21, wherein the angular ranges defined by an angle a that is the angle between a neck axis of the femur and a radial ray which runs from a center point of a circle corresponding to the femur head and through a point on the circle at which the bone contour first deviates from the spherical shape.

23. The method according to claim 19, wherein the standardized reference data for the joint is reference model data.

24. The method according to claim 19, further comprising correcting the reference data on the basis of joint-type or joint bone-type data, including at least one of antetorsion angles, retroversion angles, CCD angles, location of the front/mid-sagittal pelvic plane, or pelvic inclination.

25. The method according to claim 19, further comprising automatically selecting a suitable reference data model on the basis of the acquired patient data set.

26. The method according to claim 1, which is used for a hip joint, a shoulder joint or a knee joint.

27. A non-transitory computer readable medium comprising computer executable instructions adapted to perform a method in accordance with claim 1.

28. A computer-assisted planning method for reconstructing changes in shape on joint bones, comprising the following steps:
    acquiring a three-dimensional patient data set;
    prior to segmenting the three-dimensional patient data set, directly assigning reconstruction-type model data to the patient data set;
    determining, using a processor, resection auxiliary regions by means of the model data; and
    visually outputting the resection auxiliary regions and/or visualizing the resection auxiliary regions together with the patient data set.

* * * * *